(12) United States Patent
Lonkadi

(10) Patent No.: US 11,446,091 B2
(45) Date of Patent: Sep. 20, 2022

(54) METHOD AND SYSTEM FOR DETERMINING A NAVIGATION PATHWAY FOR INVASIVE MEDICAL INSTRUMENT IN BLOOD VESSELS

(71) Applicant: Siemens Healthcare GmbH, Erlangen (DE)

(72) Inventor: Sham S Lonkadi, Bangalore (IN)

(73) Assignee: Siemens Healthcare GmbH, Erlangen (DE)

( * ) Notice: Subject to any disclaimer, the term of this patent is extended or adjusted under 35 U.S.C. 154(b) by 313 days.

(21) Appl. No.: 16/728,427

(22) Filed: Dec. 27, 2019

(65) Prior Publication Data
US 2020/0214767 A1    Jul. 9, 2020

(30) Foreign Application Priority Data
Jan. 4, 2019   (EP) .................... 19150348

(51) Int. Cl.
| | |
|---|---|
| *A61B 5/00* | (2006.01) |
| *A61B 34/10* | (2016.01) |
| *A61B 34/20* | (2016.01) |
| *G06T 7/73* | (2017.01) |
| *G16H 30/20* | (2018.01) |
| *A61B 6/00* | (2006.01) |
| *G06T 7/00* | (2017.01) |

(52) U.S. Cl.
CPC .............. *A61B 34/10* (2016.02); *A61B 6/504* (2013.01); *A61B 34/20* (2016.02); *G06T 7/0016* (2013.01); *G06T 7/75* (2017.01); *G16H 30/20* (2018.01); *A61B 2034/107* (2016.02); *G06T 2207/30101* (2013.01)

(58) Field of Classification Search
CPC combination set(s) only.
See application file for complete search history.

(56) References Cited

U.S. PATENT DOCUMENTS

| | | |
|---|---|---|
| 6,647,093 B2 | 11/2003 | Schmitz |
| 2002/0150211 A1 | 10/2002 | Schmitz |
| (Continued) | | |

FOREIGN PATENT DOCUMENTS

WO    WO2005020148 A1    3/2005

OTHER PUBLICATIONS

European Search Report for European Application No. 19150348.1-1122 dated Jul. 12, 2019.

(Continued)

*Primary Examiner* — Joel F Brutus
(74) *Attorney, Agent, or Firm* — Lempia Summerfield Katz LLC (57) ABSTRACT

A method and system are provided for determining a navigation pathway for an invasive medical instrument in a blood vessel is provided. The method includes receiving a first medical image. The method further includes determining one or more parameters associated with the first medical image. Additionally, the method includes identifying a second medical image in a computer memory, based on the determined one or more parameters. Furthermore, the method includes modifying the second medical image based on the first medical image. The method also includes determining from the modified second medical image the navigation pathway for the invasive medical instrument.

17 Claims, 4 Drawing Sheets

(56) References Cited

U.S. PATENT DOCUMENTS

| | | |
|---|---|---|
| 2008/0071142 A1* | 3/2008 | Gattani ............ A61B 5/065 600/117 |
| 2010/0121181 A1 | 5/2010 | Wang |
| 2012/0183189 A1 | 7/2012 | Florent |
| 2014/0371578 A1 | 12/2014 | Auvray |
| 2015/0179148 A1 | 6/2015 | Auvray |
| 2015/0265179 A1* | 9/2015 | Lonkadi ............ A61B 5/061 600/424 |
| 2015/0279013 A1 | 10/2015 | Goossen |
| 2018/0068437 A1 | 3/2018 | Bronkalla |
| 2018/0158209 A1 | 6/2018 | Fine |

OTHER PUBLICATIONS

Groher, Martin, 2D-3D Registration of Vascular Images Towards 3D-Guided Catheter Interventions, Dissertation Fechnische Universität München, Fakultät für Informatik; Mar. 18, 2008; pp. 1-171; URL:https://mediatum.ub.tum.de/doc/648193/648193.pdf.

* cited by examiner

METHOD AND SYSTEM FOR DETERMINING A NAVIGATION PATHWAY FOR INVASIVE MEDICAL INSTRUMENT IN BLOOD VESSELS

CROSS REFERENCE TO RELATED APPLICATIONS

This application claims the benefit of EP19150348.1, filed on Jan. 4, 2019, which is hereby incorporated by reference in its entirety.

FIELD

Embodiments relate to a method and system for processing a medical image.

BACKGROUND

Incidences of cardiac imaging procedures are on the rise in modern times. This may be caused due to vascular damage caused due to vascular ailments such as stenosis or restenosis. Medical procedures such as balloon angioplasty may cause restenosis in patients thereby raising a need for another angioplasty procedure to correct the vascular damage. Recurrence of the vascular ailments may require the patient to undergo several imaging procedures to treat the abnormality. Each imaging procedure may require the patient to be exposed to X-ray radiation. Multiple imaging procedures may be harmful to the patient as the overall radiation dose received by the patient increases. Current mechanisms to reduce X-ray exposure to the patient may involve reducing the X-ray dose provided to the patient during image acquisition process. This may, however, still expose the patient to harmful X-ray radiation. There is no mechanism that uses medical images obtained from previous imaging procedures in a current imaging procedure to reduce X-ray exposure to the patient.

BRIEF SUMMARY AND DESCRIPTION

The scope of the present invention is defined solely by the appended claims and is not affected to any degree by the statements within the summary. The present embodiments may obviate one or more of the drawbacks or limitations in the related art.

Embodiments reduce exposure to X-ray radiation for a patient during a medical imaging procedure.

Embodiments include a method and a system for determining a navigation pathway for an invasive medical instrument in a blood vessel that uses a medical image obtained from a previous medical imaging procedure.

A method of determining a navigation pathway for an invasive medical instrument in a blood vessel is provided. The method includes receiving by a processor, a first medical image. The first medical image may be, for example, a fluoroscopic X-ray image. The first medical image may be acquired using an image acquisition device that may be used to image a patient. The method further includes determining by the processor, one or more parameters associated with the first medical image. The one or more parameters associated with the first medical image may define the properties of the first medical image. For example, the one or more parameters may correspond to one or more objects associated with the patient to be imaged. In an embodiment, the one or more parameters associated with the first medical image may include position of the patient being imaged, position coordinates associated with the imaging device, angular position of the imaging device, and/or distance between a patient table and the imaging device. The one or more parameters associated with the first medical image provide accurate identification of the object being imaged by the imaging device. The method further includes identifying by the processor, a second medical image. The second medical image may be located, for example, in a computer memory such as a storage unit. The second medical image may be identified based on the one or more parameters associated with the first medical image. The one or more parameters associated with the first medical image provide accurate identification of the second medical image. In an embodiment, the one or more parameters associated with the first medical image may match with the one or more parameters of the second medical image. Identification of the second medical image based on the one or more parameters associated with the first medical image provides accurate mapping of the first medical image with the second medical image. If the one or more parameters of the first and second medical images match, the imaged object in the first and the second medical image may be identical. Accuracy in the imaging procedure is provided. The method further includes modifying by the processor, the second medical image based on the first medical image. In an embodiment, the second medical image may have one or more differences over the first medical image. The differences may be with respect to the imaged object in the first and the second medical images. The second medical image may be modified with respect to the first medical image to provide the differences between the imaged object in the first medical image and the imaged object in the second medical image are overcome. The method further includes determining from the modified second medical image the navigation pathway for the invasive medical instrument, in the blood vessel. The use of the modified second medical image to determine the navigation pathway provides a physician to perform a medical procedure on the patient using the previously acquired medical image. The need to obtain a new medical image to perform the medical procedure is avoided. The use of the modified second medical image to perform the medical procedure provides reduction in radiation exposure to the patient.

The navigation pathway may be determined using methods known to a person skilled in the art. For example, the navigation pathway may follow a blood vessel or a centerline of a blood vessel. For example, the navigation pathway may be determined as the shortest connection from a starting point to the point of interest. For example, the navigation pathway may be determined by determined by constraints related to vessel curvature or diameter. For example, the navigation pathway may be determined by avoiding vessel curves below a minimum curve radius. For example, the navigation pathway may be determined by avoiding vessels with a diameter below a minimum vessel diameter. In an embodiment, the navigation pathway is determined using an edge detection algorithm. The edge detection algorithm provides identification of one or more edges associated with the blood vessel. The one or more edges may correspond to a structure of blood vessel using which the navigation pathway for the invasive medical instrument may be determined. In a further embodiment, a centerline of the blood vessel may be determined that may correspond to the navigation pathway in the blood vessel.

In an embodiment of the method, the one or more parameters associated with the first medical image include one or more of position of the patient being imaged, position coordinates associated with the imaging device, angular position of the imaging device, and distance between the patient table and the imaging device. The one or more parameters associated with the first medical image provide the accurate imaging information associated with the first medical image. Accurate identification of the second medical image is achieved.

According to an embodiment of the method, the second medical image may be obtained from a medical database. The second medical image may be acquired during a previous medical imaging procedure. The medical database may be a repository which includes one or more medical images and associated medical data sets. In an embodiment, the second medical image may be associated with the same patient as that of the first medical image. Accuracy in the medical procedure is thus provided.

In an embodiment of the method, in identifying the second medical image based on the one or more parameters, the method includes identifying by the processor, one or more medical images based on the one or more parameters associated with the first medical image. The one or more medical images may be identified from the plurality of medical images located in the medical database. The one or more parameters associated with the first medical image provide identification of one or more medical images that may be associated with one or more parameters similar to the one or more parameters associated with the first medical image. For example, if the parameter is distance between the patient table and the imaging device, the distance between the patient table and the imaging device in the first medical image may be similar to the distance between the patient table and the imaging device in the one or more medical images identified from the medical database. The method further includes identifying one or more objects from the first medical image. The one or more objects may be, for example, but not limited to, the blood vessel of the patient being imaged. The method further includes identifying one or more objects from the one or more identified medical images. The identification of one or more objects in the medical images may be achieved, for example, using an edge detection algorithm. In an embodiment, one or points in the first medical image and the one or more medical images are identified at which image intensity may change sharply. The one or more points may be organized into line segments to detect the edge of the one or more objects in the medical images. The method further includes comparing the one or more objects in the first medical image with the one or more objects in the one or more medical images. In an embodiment, the one or more objects identified in the first medical image may be overlapped on the one or more objects identified in the one or more medical images. Overlapping the one or more objects in the first medical image on the one or more objects in the one or more medical images provides accurate identification of the second medical image from the one or more medical images. The identification may be based on the similarities between the objects in the first medical image and the objects in at least one of the one or more medical images. In an embodiment, a Hausdorff distance between the overlapping one or more objects may be calculated to identify the most accurate second medical image. The method further includes determining the second medical image from the one or more medical images based on the comparison between the overlapping one or more objects. The Hausdorff distance measures how far two subsets of a metric space are from each other. Calculating the Hausdorff distance between the overlapping objects in the medical images provides identification of the medical image that is the most similar to the first medical image. The most similar medical image to the first medical image may be determined as the second medical image.

According to another embodiment of the method, modifying the second medical image based on the first medical image includes determining a structural orientation of the one or more objects in the first medical image. In an embodiment, the one or more objects, i.e. the blood vessel, in the first medical image may include a defined structural orientation. Blood vessels may include three possible structural orientations in a two-dimensional image. The first structural orientation of the blood vessel may be along a horizontal axis, i.e. X-axis of the medical image. The second structural orientation of the blood vessel may be along a vertical axis, i.e. Y-axis of the medical image. The third structural orientation of the blood vessel may include the blood vessel at an angle with the X-axis of the medical image. The structural orientation of the blood vessel in the patient may vary with respect to time and movement. Alternatively, the structural orientation of the blood vessel may also change due to a previous medical procedure performed on the blood vessel or in the vicinity of the blood vessel. Determination of the structural orientation of the blood vessel provides accurate identification of the navigation pathway in the blood vessel. The method further includes determining a structural orientation of one or more objects in the second medical image. A deviation between the structural orientation of the one or more objects in the first medical image and the one or more objects in the second medical image is identified. In an embodiment, the deviation in the structural orientation between the one or more objects in the first and the second medical image may be identified, for example, using pattern matching algorithm. The pattern of the one or more objects in the first medical image is matched with the pattern of the one or more objects in the second medical image. A deviation may be identified if the pattern of at least one portion of the one or more objects in the first medical image does not match with corresponding pattern of the one or more objects in the second medical image. The deviation in the structural orientation of the one or more objects in the first medical image may exist in comparison to the structural orientation of the one or more objects in the second medical image due to, for example, a previous medical procedure performed on the one or more objects. The method further includes correcting the structural orientation of the one or more objects in the second medical image based on the structural orientation of the one or more objects in the first medical image. The correction may be performed if the deviation is identified. In an embodiment, the correction on the second medical image may be performed using one or more machine learning techniques. The one or more objects in the second medical image may be corrected, for example, by modifying the pixels associated with the one or more objects in the second medical image. One or more pixels associated with the one or more objects may be selected for manipulation. The manipulation may include modifying the pixel values of the one or more pixels with respect to the corresponding pixels in the first medical image. In an embodiment, the one or more objects in the second medical image may be, for example, scaled or warped based on pixel modification. The modified second medical image is identical to the first medical image. The determination of the navigation pathway in the blood vessel is provided accurately.

In an embodiment of the method, one or more subsequent medical images may be calibrated based on the modified second medical image. The one or more subsequent medical images may be acquired by the imaging device after acquisition of the second medical image. In an embodiment, the one or more subsequent medical images may need calibration based on the modified second medical image. The calibration may include, for example, structural alignment of one or more objects in the one or more subsequent medical images with respect to the one or more objects in the modified second medical image. Structural alignment of the one or more objects in the one or more subsequent medical images may include, for example, mapping edges of the one or more objects in the one or more subsequent medical images with the edges of the one or more objects in the modified second medical image. The method further includes determining by the processor, a critical point in the navigation pathway in the blood vessel. Blood vessels may branch into several smaller vessels that carry blood to one or more organs and back to heart. A point at which the blood vessel branches out may be identified as a critical point. The navigation of the invasive medical instrument at a branching point may have to be performed with utmost care. An error in navigation process may be detrimental to the blood vessel and to the health of the patient. Such branching points in the blood vessel are identified as critical points. Additionally, the physician may have to indicate which branch of the blood vessel may be used for further navigation. The increases the criticality of the branching point. The first medical image and the second medical image may be analyzed to determine if the critical point has been reached in the blood vessel. Alternatively, the critical point may also include points in the blood vessel where a change in the vessel diameter is observed, for example, the blood vessel becomes narrow. The change in the vessel diameter may be, for example, due to blockage of the blood vessel. The determination of critical point(s) in the blood vessel provides identification of risks in the navigation pathway. Safety of the patient is ensured during the medical procedure.

According to another embodiment, the method further includes determining if a new medical image is to be acquired by the imaging device based on the identification of the critical point in the navigation pathway. Acquisition of the new medical image provides accurate navigation of the invasive medical instrument in the blood vessel. The new medical image provides determination of the current position of the invasive medical instrument in the blood vessel and provides guidance to the physician on the path to be followed at the critical point.

In an embodiment of the method, the first medical image is received from the imaging device. Alternatively, the first medical image may also be obtained from the medical database.

In an embodiment of the method, in calibrating the one or more subsequent medical images based on the second modified medical image includes determining a structural orientation of one or more objects in the one or more subsequent medical images. In an embodiment, the one or more objects, i.e. the blood vessel, in the one or more subsequent medical images may have a defined structural orientation. Blood vessels may have three possible structural orientations in a two-dimensional image. The first structural orientation of the blood vessel may be along a horizontal axis, i.e. X-axis of the medical image. The second structural orientation of the blood vessel may be long a vertical axis, i.e. Y-axis of the medical image. The third structural orientation of the blood vessel may include the blood vessel at an angle with the X-axis of the medical image. The structural orientation of the blood vessel in the patient may vary with respect to time and movement. Alternatively, the structural orientation of the blood vessel may also change due to a previous medical procedure performed on the blood vessel or in the vicinity of the blood vessel. Determination of the structural orientation of the blood vessel provides accurate identification of the navigation pathway in the blood vessel. The method further includes determining a structural orientation of one or more objects in the modified second medical image. A deviation between the structural orientation of the one or more objects in the one or more subsequent medical images and the one or more objects in the modified second medical image is identified. In an embodiment, the deviation in the structural orientation may be identified, for example, using pattern matching algorithm. The pattern of the one or more objects in the one or more subsequent medical images is matched with the pattern of the one or more objects in the modified second medical image. A deviation may be identified if the pattern of at least one portion of the one or more objects in the subsequent medical image does not match with corresponding pattern of the one or more objects in the modified second medical image. The deviation in the structural orientation of the one or more objects in the subsequent medical image may exist in comparison to the structural orientation of the one or more objects in the modified second medical image due to, for example, a previous medical procedure performed on the one or more objects. The method further includes correcting the structural orientation of the one or more objects in the subsequent medical image based on the structural orientation of the one or more objects in the modified second medical image. The correction may be performed if the deviation is identified. In an embodiment, the correction on the second medical image may be performed using one or more machine learning techniques. The one or more objects in the subsequent medical image may be corrected, for example, by modifying the pixels associated with the one or more objects in the subsequent medical image. One or more pixels associated with the one or more objects may be selected for manipulation. The manipulation may include modifying the pixel values of the one or pixels with respect to the corresponding pixels in the modified second medical image. In an embodiment, the one or more objects in the subsequent medical image may be, for example, scaled or warped based on pixel modification. In an embodiment, the corrected subsequent medical image may be the second modified medical image for the next subsequent medical image to be calibrated from a set of one or more subsequent medical images. The one or more subsequent medical images are calibrated based on the modified second medical image. The determination of the navigation pathway in the blood vessel is provided accurately.

The disclosed method may also be used to reduce radiation exposure to patients from different image acquisition devices such as tomographic MRI, CT, PET and/or SPECT imaging devices. The first medical image may also be, for example, tomographic MRI, CT, or a PET scan images that include the one or more imaged objects. The disclosed method steps may be applicable to images acquired from the other image acquisition devices. In an embodiment, the one or more objects in the medical image may include tissues and/or organs that are tubular in nature, such as, but not limited to, the intestine, trachea, esophagus, etc. The method steps as disclosed above may be configured to determine a navigation pathway in any tissue and/organ that may have a lumen.

Embodiments include a system for determining a navigation pathway for an invasive medical instrument in a blood vessel.

In an embodiment, the system includes a processor, a medical database coupled to the processor, a memory coupled to the processor, the memory including a navigation module. The navigation module is configured to receive a first medical image. The first medical image may be, for example, a fluoroscopic X-ray image. The first medical image may be acquired using an image acquisition device that may be used to image a patient. The navigation module is further configured to determine one or more parameters associated with the first medical image. The one or more parameters associated with the first medical image may define the properties of the first medical image. For example, the one or more parameters may correspond to one or more objects associated with the patient to be imaged. In an embodiment, the one or more parameters associated with the first medical image may include position of the patient being imaged, position coordinates associated with the imaging device, angular position of the imaging device, and/or distance between a patient table and the imaging device. The one or more parameters associated with the first medical image provide accurate identification of the object imaged by the imaging device. The navigation module is further configured to identify a second medical image. The second medical image may be located, for example, in a computer memory such as a storage unit. The second medical image may be identified based on the one or more parameters associated with the first medical image. The one or more parameters associated with the first medical image provide accurate identification of the second medical image. In an embodiment, the one or more parameters associated with the first medical image may match with the one or more parameters of the second medical image. Identification of the second medical image based on the one or more parameters associated with the first medical image provides accurate mapping of the first medical image with the second medical image. If the one or more parameters of the first and second medical images match, the imaged object in the first and the second medical image may be identical. Accuracy in the imaging procedure is provided. The navigation module is further configured to modify the second medical image based on the first medical image. In an embodiment, the second medical image may have one or more differences over the first medical image. The differences may be with respect to the imaged object in the first and the second medical images. The second medical image may be modified with respect to the first medical image to ensure the differences in the imaged object in the first medical image and the imaged object in the second medical image are overcome. The navigation module is further configured to determine from the modified second medical image the navigation pathway for the invasive medical instrument, in the blood vessel. The use of the modified second medical image to determine the navigation pathway provides a physician to perform a medical procedure on the patient using the previously acquired medical image. The need to obtain a new medical image to perform the medical procedure is avoided. The use of the modified second medical image to perform the medical procedure provides reduction in radiation exposure to the patient.

The navigation pathway may be determined using methods known to a person skilled in the art. For example, the navigation pathway may follow a blood vessel or a centerline of a blood vessel. For example, the navigation pathway may be determined as the shortest connection from a starting point to the point of interest. For example, the navigation pathway may be determined by determined by constraints related to vessel curvature or diameter. For example, the navigation pathway may be determined by avoiding vessel curves below a minimum curve radius. For example, the navigation pathway may be determined by avoiding vessels with a diameter below a minimum vessel diameter. In an embodiment, the navigation pathway is determined using an edge detection algorithm. The edge detection algorithm provides identification of one or more edges associated with the blood vessel. The one or more edges may correspond to a structure of blood vessel using which the navigation pathway for the invasive medical instrument may be determined. In an embodiment, a centerline of the blood vessel may be determined that may correspond to the navigation pathway in the blood vessel.

In an embodiment, the one or more parameters associated with the first medical image include one or more of position of the patient being imaged, position coordinates associated with the imaging device, angular position of the imaging device, and distance between the patient table and the imaging device. The one or more parameters associated with the first medical image provide the accurate imaging information associated with the first medical image. Accurate identification of the second medical image is achieved.

In an embodiment, the second medical image may be obtained from the medical database. The second medical image may be acquired during a previous medical imaging procedure. The medical database may be a repository that includes one or more medical images and associated medical data sets. In an embodiment, the second medical image may be associated with the same patient as that of the first medical image providing accuracy in the medical procedure.

In an embodiment, in identifying the second medical image based on the one or more parameters, the navigation module is further configured to identify one or more medical images based on the one or more parameters associated with the first medical image. The one or more medical images may be identified from the plurality of medical images located in the medical database. The one or more parameters associated with the first medical image provide identification of one or more medical images that may be associated with one or more parameters similar to the one or more parameters associated with the first medical image. For example, if the parameter is distance between the patient table and the imaging device, the distance between the patient table and the imaging device in the first medical image may be similar to the distance between the patient table and the imaging device in the one or more medical images identified from the medical database. The navigation module is further configured to identify one or more objects from the first medical image. The one or more objects may be, for example, but not limited to, the blood vessel of the patient being imaged. The navigation module is further configured to identify one or more objects from the one or more identified medical images. The identification of one or more objects in the medical images may be achieved, for example, using an edge detection algorithm. In an embodiment, one or points in the first medical image and the one or more medical images are identified at which image intensity may change sharply. The one or more points may be organized into line segments to detect the edge of the one or more objects in the medical images. The navigation module is further configured to compare the one or more objects in the first medical image with the one or more objects in the one or more medical images. In an embodiment, the one or more objects identified in the first medical image may be overlapped on the one or more objects identified in the one or more medical images. Overlapping the one or more objects in the first medical image on the one or more objects in the one or more medical images provides accurate identification of the second medical image from the one or more medical images. The identification may be based on the similarities between the objects in the first medical image and the objects in at least one of the one or more medical images. In an embodiment, a Hausdorff distance between the overlapping one or more objects may be calculated to identify the most accurate second medical image. The navigation module is further configured to determine the second medical image from the one or more medical images based on the comparison between the overlapping one or more objects. The Hausdorff distance measures how far two subsets of a metric space are from each other. Calculating the Hausdorff distance between the overlapping objects in the medical images provides identification of the medical image that is the most similar to the first medical image. The most similar medical image to the first medical image may be determined as the second medical image.

In an embodiment, in modifying the second medical image based on the first medical image, the navigation module is further configured to determine a structural orientation of the one or more objects in the first medical image. In an embodiment, the one or more objects, i.e. the blood vessel, in the first medical image may include a defined structural orientation. Blood vessels may include three possible structural orientations in a two-dimensional image. The first structural orientation of the blood vessel may be along a horizontal axis, i.e. X-axis of the medical image. The second structural orientation of the blood vessel may be along a vertical axis, i.e. Y-axis of the medical image. The third structural orientation of the blood vessel may include the blood vessel at an angle with the X-axis of the medical image. The structural orientation of the blood vessel in the patient may vary with respect to time and movement. Alternatively, the structural orientation of the blood vessel may also change due to a previous medical procedure performed on the blood vessel or in the vicinity of the blood vessel. Determination of the structural orientation of the blood vessel provides accurate identification of the navigation pathway in the blood vessel. The navigation module is further configured to determine a structural orientation of one or more objects in the second medical image. A deviation between the structural orientation of the one or more objects in the first medical image and the one or more objects in the second medical image is identified. In an embodiment, the deviation in the structural orientation between the one or more objects in the first and the second medical image may be identified, for example, using pattern matching algorithm. The pattern of the one or more objects in the first medical image is matched with the pattern of the one or more objects in the second medical image. A deviation may be identified if the pattern of at least one portion of the one or more objects in the first medical image does not match with corresponding pattern of the one or more objects in the second medical image. The deviation in the structural orientation of the one or more objects in the first medical image may exist in comparison to the structural orientation of the one or more objects in the second medical image due to, for example, a previous medical procedure performed on the one or more objects. The navigation module is further configured to correct the structural orientation of the one or more objects in the second medical image based on the structural orientation of the one or more objects in the first medical image. The correction may be performed if the deviation is identified. In an embodiment, the correction on the second medical image may be performed using one or more machine learning techniques. The one or more objects in the second medical image may be corrected, for example, by modifying the pixels associated with the one or more objects in the second medical image. One or more pixels associated with the one or more objects may be selected for manipulation. The manipulation may include modifying the pixel values of the one or pixels with respect to the corresponding pixels in the first medical image. In an embodiment, the one or more objects in the second medical image may be, for example, scaled or warped based on pixel modification. The modified second medical image is identical to the first medical image. The determination of the navigation pathway in the blood vessel is provided accurately.

In an embodiment, one or more subsequent medical images may be calibrated based on the modified second medical image. The one or more subsequent medical images may be acquired by the imaging device after acquisition of the second medical image. In an embodiment, the one or more subsequent medical images may need calibration based on the modified second medical image. The calibration may include, for example, structural alignment of one or more objects in the one or more subsequent medical images with respect to the one or more objects in the modified second medical image. Structural alignment of the one or more objects in the one or more subsequent medical images may include, for example, mapping edges of the one or more objects in the one or more subsequent medical images with the edges of the one or more objects in the modified second medical image. The navigation module is further configured to determine by the processor, a critical point in the navigation pathway in the blood vessel. Blood vessels may branch into several smaller vessels that carry blood to one or more organs and back to heart. A point at which the blood vessel branches out may be identified as a critical point. The navigation of the invasive medical instrument at a branching point may have to be performed with utmost care. An error in navigation process may be detrimental to the blood vessel and to the health of the patient. The branching points are identified as critical points. Additionally, the physician may indicate which branch of the blood vessel may have to be used for further navigation which increases the criticality of the branching point. The first medical image and the second medical image may be analyzed to determine if the critical point has been reached in the blood vessel. Alternatively, the critical point may also include points in the blood vessel where a change in the vessel diameter is observed, for example, the blood vessel becomes narrow. The change in the vessel diameter may be, for example, due to blockage of the blood vessel. Determination of critical point(s) in the blood vessel provides identification of risks in the navigation pathway. Safety of the patient is provided during the medical procedure.

In an embodiment, the navigation module is further configured to determine if a new medical image is to be acquired by the imaging device based on the identification of the critical point in the navigation pathway. Acquisition of the new medical image provides accurate navigation of the invasive medical instrument in the blood vessel. The new medical image provides determination of the current position of the invasive medical instrument in the blood vessel and provides guidance to the physician on the path to be followed at the critical point.

In an embodiment, the first medical image is received from the imaging device. Alternatively, the first medical image may also be obtained from the medical database.

In an embodiment, in calibrating the one or more subsequent medical images based on the second modified medical image, the navigation module is configured to determine a structural orientation of one or more objects in the one or more subsequent medical images. In an embodiment, the one or more objects, i.e. the blood vessel, in the one or more subsequent medical images may include a defined structural orientation. Blood vessels may include three possible structural orientations in a two-dimensional image. The first structural orientation of the blood vessel may be along a horizontal axis, i.e. X-axis of the medical image. The second structural orientation of the blood vessel may be along a vertical axis, i.e. Y-axis of the medical image. The third structural orientation of the blood vessel may include the blood vessel at an angle with the X-axis of the medical image. The structural orientation of the blood vessel in the patient may vary with respect to time and movement. Alternatively, the structural orientation of the blood vessel may also change due to a previous medical procedure performed on the blood vessel or in the vicinity of the blood vessel. Determination of the structural orientation of the blood vessel provides accurate identification of the navigation pathway in the blood vessel. The navigation module is further configured to determine a structural orientation of one or more objects in the modified second medical image. A deviation between the structural orientation of the one or more objects in the one or more subsequent medical images and the one or more objects in the modified second medical image is identified. In an embodiment, the deviation in the structural orientation may be identified, for example, using pattern matching algorithm. The pattern of the one or more objects in the one or more subsequent medical images is matched with the pattern of the one or more objects in the modified second medical image. A deviation may be identified if the pattern of at least one portion of the one or more objects in the subsequent medical image does not match with corresponding pattern of the one or more objects in the modified second medical image. The deviation in the structural orientation of the one or more objects in the subsequent medical image may exist in comparison to the structural orientation of the one or more objects in the modified second medical image due to, for example, a previous medical procedure performed on the one or more objects. The navigation module is further configured to correct the structural orientation of the one or more objects in the subsequent medical image based on the structural orientation of the one or more objects in the modified second medical image. The correction may be performed if the deviation is identified. In an embodiment, the correction on the second medical image may be performed using one or more machine learning techniques. The one or more objects in the subsequent medical image may be corrected, for example, by modifying the pixels associated with the one or more objects in the subsequent medical image. One or more pixels associated with the one or more objects may be selected for manipulation. The manipulation may include modifying the pixel values of the one or pixels with respect to the corresponding pixels in the modified second medical image. In an embodiment, the one or more objects in the subsequent medical image may be, for example, scaled or warped based on pixel modification. The one or more subsequent medical images are calibrated based on the modified second medical image. The determination of the navigation pathway in the blood vessel is provided accurately.

In an alternative embodiment, the one or more objects in the medical image may include tissues and/or organs that are tubular in nature, such as, but not limited to, intestine, trachea, esophagus, etc. The navigation module may be configured to perform the method steps as disclosed above to determine a navigation pathway in any tissue and/organ that may have a lumen.

Embodiments include a computer program product including a computer program, the computer program configured to be loadable into a storage unit of a system, including program code sections to make the system execute the method according to an aspect when the computer program is executed in the system.

Embodiments include a computer-readable medium, on which program code sections of a computer program are saved, the program code sections configured to be loadable into and/or executable in a system to make the system execute the method according to an aspect when the program code sections are executed in the system.

The realization by a computer program product and/or a computer-readable medium includes an advantage that already existing management systems may be easily adopted by software updates in order to work.

The computer program product may be, for example, a computer program or include another element apart from the computer program. The other element may be hardware, for example a memory device, on which the computer program is stored, a hardware key for using the computer program and the like, and/or software, for example a documentation or a software key for using the computer program.

DETAILED DESCRIPTION

Figure 1:
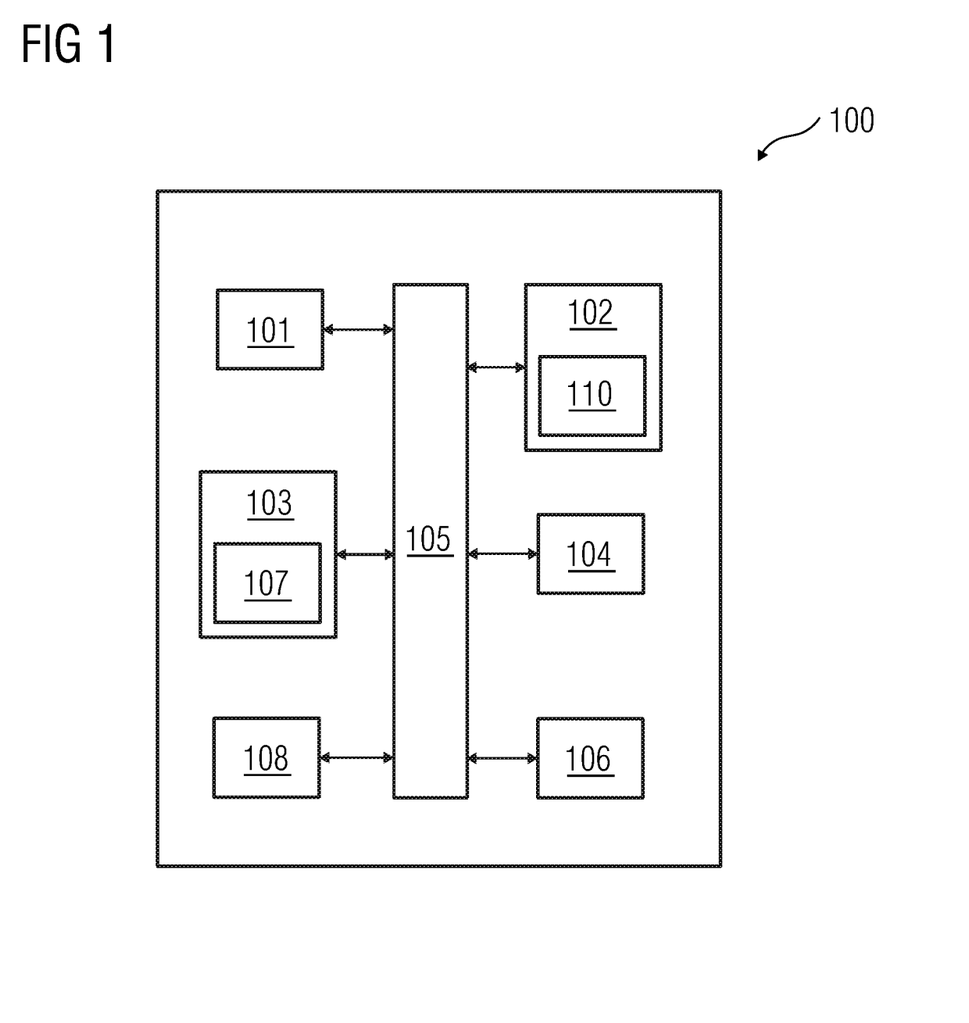
FIG. 1 depicts a block diagram of a data processing system in which an embodiment for determining a navigation pathway for an invasive medical instrument in a blood vessel may be implemented.

FIG. 1 is a block diagram of a data processing system 100 in which an embodiment may be implemented, for example, as a system 100 determining a navigation pathway for an invasive medical instrument in a blood vessel, configured to perform the processes as described therein. In FIG. 1, the data processing system 100 includes a processor 101, a memory 102, a storage unit 103, an input unit 104, an output unit 106, a bus 105, and a network interface 108.

The processor 101 may be any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processor 101 may also include embedded controllers, such as generic or programmable logic devices or arrays, application specific integrated circuits, single-chip computers, and the like.

The memory 102 may be volatile memory and non-volatile memory. The memory 102 may be coupled for communication with the processor 101. The processor 101 may execute instructions and/or code stored in the memory 102. A variety of computer-readable storage media may be stored in and accessed from the memory 102. The memory 102 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 201 includes a navigation module 110 stored in the form of machine-readable instructions on any of the above-mentioned storage media and may be in communication to and executed by processor 101. When executed by the processor 101, the navigation module 108 causes the processor 101 to determine a navigation pathway for a n invasive medical instrument in a blood vessel. Method steps executed by the processor 101 to achieve the abovementioned functionality are elaborated upon in detail in FIGS. 2, 3, 4, 5 and 6.

The storage unit 103 may be a non-transitory storage medium that stores a medical database 107. The medical database 107 is a repository of medical images and associated medical data sets related to one or more patients that is maintained by a healthcare service provider. The input unit 104 may include a keypad, a touch-sensitive display, a camera (such as a camera receiving gesture-based inputs), etc. configured to receive input signal such as a medical image. The bus 105 acts as interconnect between the processor 101, the memory 102, the storage unit 103, the input unit 204, the output unit 106 and the network interface 108.

The hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter also may be used in addition or in place of the hardware depicted. The depicted example is provided for the purpose of explanation only and is not meant to imply architectural limitations with respect to the present disclosure.

A data processing system 100 in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through a pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Wash. may be employed if suitably modified. The operating system is modified or created in accordance with the present disclosure as described.

Disclosed embodiments provide systems and methods for processing medical images. The systems and methods may determine a navigation pathway for invasive medical instruments in blood vessels.

Figure 2:
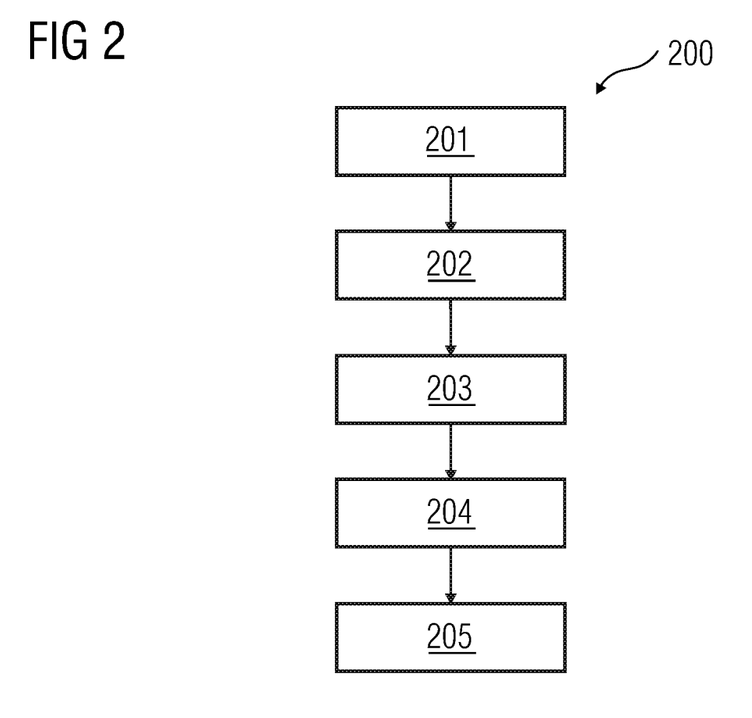
FIG. 2 depicts a flowchart of a method of determining a navigation pathway for an invasive medical instrument in a blood vessel, according to an embodiment.

FIG. 2 depicts a flowchart of a method 200 of determining a navigation pathway for an invasive medical instrument in a blood vessel, according to an embodiment. In an embodiment, the invasive medical instrument is a guidewire. The guidewire is a medical instrument or a device that provides inserting, positioning and movement of a catheter in a patient's body. The guidewire may be passed through a measuring device that may detect the motion of the guidewire in the patient's body. The measuring device may be configured to measure the distance traversed by the guidewire in the patient's body. At step 201, the method 200 includes receiving a first medical image. The first medical image may include one or more objects. The one or more objects may be the blood vessel in which the guidewire is to be inserted and navigated. The first medical image may be, for example an X-ray fluoroscopic image acquired from an X-ray imaging device. In an embodiment, the first medical image may be obtained from a medical database 107. At step 202, one or more parameters associated with the first medical image is determined. The one or more parameters may include a position of the patient being imaged, position coordinates associated with the imaging device, angular position of the imaging device, and/or distance between a patient table and the imaging device. The one or more parameters associated with the first medical image provides determination of properties of the one or more objects in the first medical image. If the imaging device is positioned at an angle with respect to the patient position, the one or more objects in the first medical image may be imaged from the angular perspective. The properties of the one or more objects in the medical image may change based on a change in the one or more parameters associated with the medical image. At step 203, the method 200 includes identifying a second medical image based on the one or more parameters associated with the first medical image. In an embodiment, the second medical image may be located in the medical database 107. The second medical image may have been acquired by the imaging device during a previous medical procedure performed on the same patient. The second medical image also includes one or more imaged objects. The one or more objects may be the blood vessel through which the guidewire is to be navigated. The method steps for identification of the second medical image based on the one or more parameters are described in FIG. 3.

At step 204 of method 200, the second medical image is modified based on the first medical image. In an embodiment, the one or more objects in the second medical image may be modified with respect to the one or more objects in the first medical image. The modification may be performed if a deviation is identified between the one or more objects in the first medical image and the one or more objects in the second medical image. The method steps describing the modification of the one or more objects in the second medical image are detailed in FIG. 4. At step 205, the navigation pathway for the invasive medical instrument is determined from the modified second medical image. The navigation of the guidewire in the patient's body is achieved using a previously acquired medical image. Use of a previously acquired medical image for determining the navigation pathway for the invasive medical instrument in the blood vessel provides reduction of X-ray exposure to the patient.

In an embodiment, the navigation pathway is determined using an edge detection algorithm. The edge detection algorithm provides identification of one or more edges associated with the blood vessel. The one or more edges may correspond to a structure of blood vessel using which the navigation pathway for the invasive medical instrument may be determined. In a further embodiment, a centerline of the blood vessel may be determined that may correspond to the navigation pathway in the blood vessel. The centerline of the blood vessel may be determined using methods known to a person skilled in the art. For example, a point between parallel edges of the blood vessel may be considered. An average of distances between the chosen point and each of the determined edges is computed to obtain the centerline of the blood vessel. In another embodiment, the navigation pathway may be determined using a C-arm position associated with the image acquisition device. At least one of the edges of the blood vessel in the modified second medical image indicates a direction of movement of the C-arm of the image acquisition device. The blood vessel corresponding to the edge may provide identification of the navigation pathway in the modified second medical image. In a further embodiment, one or more position coordinates associated with the C-arm of the image acquisition device may provide determination of the navigation pathway in the modified second medical image. The second medical image may be associated with one or more C-arm position coordinates. The one or more C-arm position coordinates provide determination of subsequent one or more images that form a part of the navigation pathway.

Figure 3:
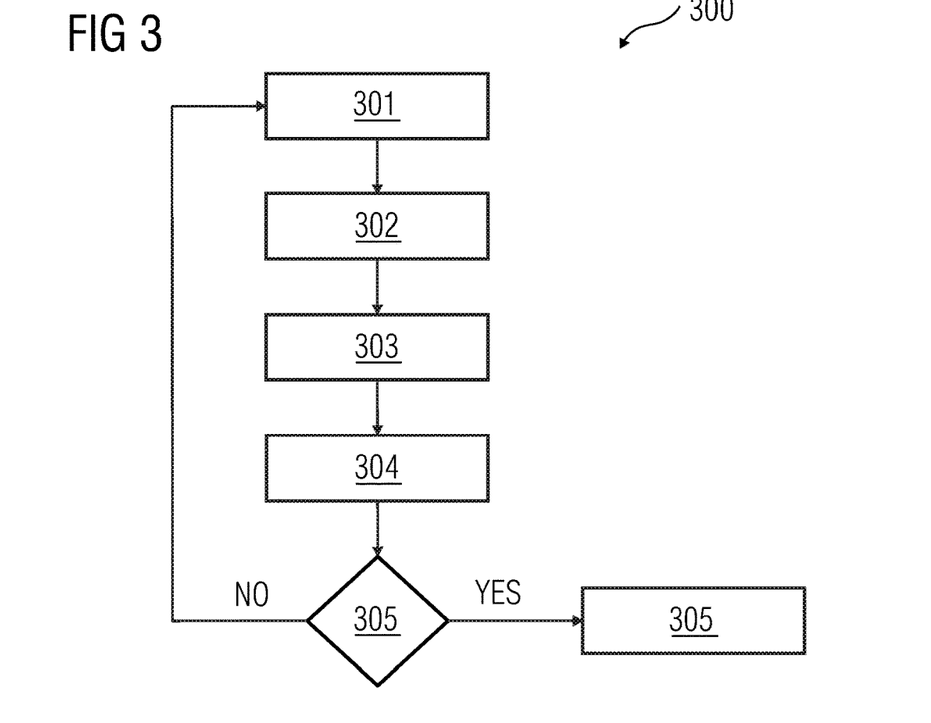
FIG. 3 depicts a flowchart of a method of identifying the second medical image based on or more parameters associated with the first medical image, according to an embodiment.

FIG. 3 depicts a flowchart of a method 300 for identifying the second medical image based on the one or more parameters associated with the first medical image. At step 301, one or more medical images are identified based on the one or more parameters associated with the first medical image. The one or more parameters provide determination of one or more properties associated with the one or more objects imaged in the first medical image. The one or more medical images may be identified from the medical database 107. The one or more medical images may also be associated with similar one or more parameters. At step 302, one or more objects are identified from the first medical image. The blood vessel imaged in the first medical image may be identified. At step 303, one or more objects in the one or more medical images is identified. In an embodiment, the identification of one or more objects in the first medical image and the one or more medical images may be performed using an edge detection algorithm. The edge detection algorithm may detect the one or more objects in the medical images based on a sharp change in image intensity at one or more points on the image. The points where the sharp change in the image intensity is identified may be connected through line segments so as to define an outline along the one or more objects in the medical images. At step 304, the one or more objects in the first medical image and the one or more objects in the one or more medical images are compared. The comparison may be performed to identify similarities between the one or more objects in the first medical image and the one or more objects in the one or more medical images. The one or more objects identified in the first medical image may be overlapped on the one or more objects identified in the one or more medical images. Overlapping the one or more objects in the first medical image on the one or more objects in the one or more medical images provides accurate identification of the second medical image from the one or more medical images. In an embodiment, the comparison may be performed using a pattern matching algorithm. A Hausdorff distance is calculated between the overlapping one or more objects to identify the most accurate second medical image. The Hausdorff distance measures how far two subsets of a metric space are from each other. Calculating the Hausdorff distance between the overlapping objects in the medical images provides identification of the medical image that is the most similar to the first medical image.

At step 305, a determination is made if the one or more objects in the first medical image match with the one or more objects in at least one of the one or more medical images. If at least one medical image of the one or more medical image matches, at step 306, the at least one medical image is identified as the second medical image. If no match is identified, one or more medical images are further identified based on the one or more parameters associated with the first medical image. The accurate identification of second medical image is provided. Only the medical images that include one or more objects similar to the one or more objects in the first medical image are identified for determination of the navigation pathway in the blood vessel. Error in navigating the invasive medical instrument in the blood vessel is reduced.

Figure 4:
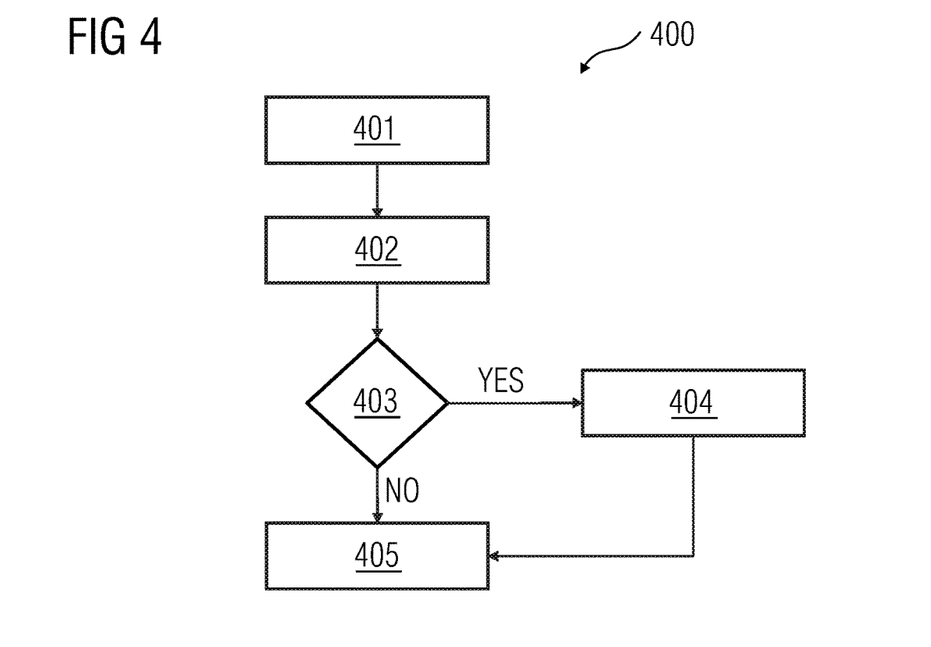
FIG. 4 depicts a flowchart of a method of modifying the second medical image based on the first medical image, according to an embodiment.

FIG. 4 illustrates a flowchart of a method 400 of modifying the second medical image based on the first medical image. At step 401, structural orientation of the one or more objects in the first medical image is determined. A blood vessel may have a defined structural orientation. Blood vessels may have three possible structural orientations in a two-dimensional image. The first structural orientation of the blood vessel may be along a horizontal axis, i.e. X-axis of the medical image. The second structural orientation of the blood vessel may be along a vertical axis, i.e. Y-axis of the medical image. The third structural orientation of the blood vessel may include the blood vessel at an angle with the X-axis of the medical image. The structural orientation of the blood vessel in the patient may vary with respect to time and movement. Alternatively, the structural orientation of the blood vessel may also change due to a previous medical procedure performed on the blood vessel or in the vicinity of the blood vessel. Determination of the structural orientation of the blood vessel provides accurate identification of the navigation pathway in the blood vessel. At step 402, a structural orientation of the one or more objects in the second medical image is determined. At step 403, a determination is made if a deviation exists between the structural orientation of the one or more objects in the first medical image and the one or more objects in the second medical image. The deviation may be identified, for example, using a pattern matching algorithm. If a deviation is identified, at step 404, the structural orientation of the one or more objects in the second medical image is corrected based on the structural orientation of the one or more objects in the first medical image. The correction may render the one or more objects in the second medical image to be similar or identical to the one or more objects in the first medical image.

In an embodiment, the one or more objects in the second medical image may be corrected by modifying the pixel values of one or more pixels in at least one portion of the one or more objects. The modification of pixel values in the second medical image may be performed based on the pixel values of the corresponding portion of the one or more objects in the first medical image. Modification of pixel values of the at least one portion of the one or more objects in the second medical image may perform scaling or warping of the one or more objects in the second medical image. The modification of the one or more objects in the second medical image provides obtaining a modified second medical image. At step 405, the modified second medical image is used to perform the medical procedure of navigating the invasive medical instrument in the blood vessel. Alternatively, if no deviation is determined at step 403, the second medical image may be used for the medical procedure without performing any modification. Modifying the second medical image with respect to the first medical image provides accurate navigation of the invasive medical instrument in the blood vessel. In an embodiment, a second medical image may not be structurally aligned with the first medical image if the blood vessel has undergone a structural deformity or change. Modifying the second medical image with respect to the first medical image prevents a physician from performing an erroneous motion of the invasive medical instrument in the blood vessel.

In an embodiment, the correction of the one or more objects in the second medical image may be achieved using a machine learning model. The machine learning model may be, for example, a neural network-based model that may be configured to identify the deviation between the one or more objects in the first medical image and the one or more objects in the second medical image. On identification of a deviation, the one or more objects in the second medical image is corrected or modified using one or more machine learning techniques. The machine learning model may employ one or more machine learning techniques to perform the correction of the one or more objects in the second medical image. In a further embodiment, the modified second medical image may be used for further training of the machine learning model to perform the modifications of one or more objects in one or more other medical images.

Figure 6:
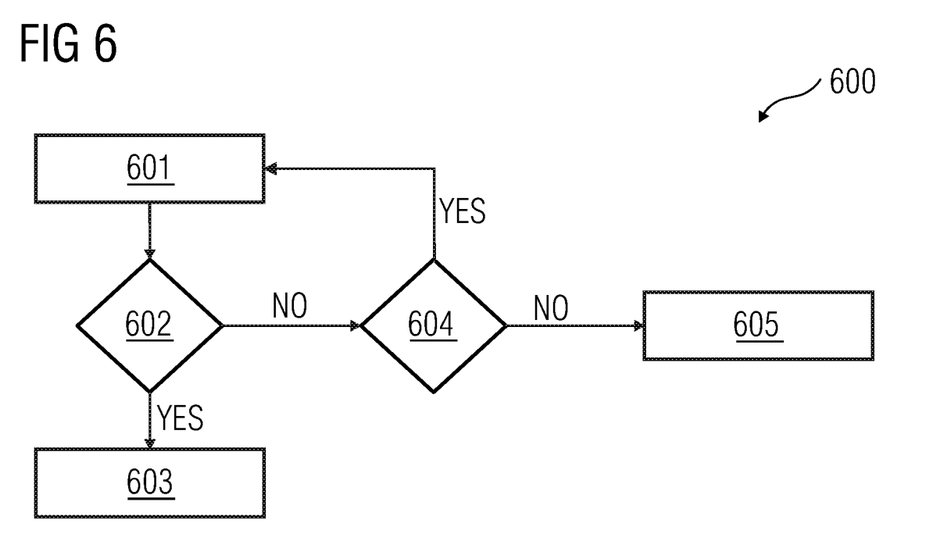
FIG. 6 depicts a flowchart of a method of determining if a new medical image is to be acquired by the imaging device, according to an embodiment.

FIG. 6 depicts a flowchart of a method 600 of determining a critical point in the navigation pathway in the blood vessel, according to an embodiment. At step 601, one or more subsequent medical images are calibrated based on the modified second medical image. The one or more subsequent medical images may have been acquired by the imaging device after the acquisition of the second medical image. The one or more subsequent medical images may depict a continuation of the blood vessel being imaged. The one or more subsequent medical images may depict the navigation pathway to be traversed by the invasive medical instrument in the blood vessel. At step 602, the calibrated one or more subsequent medical images are analyzed for a presence of a critical point in the navigation pathway in the blood vessel. In an embodiment, a critical point in a blood vessel may include, for example, a branching point where the blood vessel may split into two or more smaller vessels. Alternatively, the critical point may also include a location in the blood vessel that may be narrower due to presence of a blockage. The points in the blood vessel may be critical as the navigation of the invasive medical instrument at a branching point may have to be performed with utmost care. An error in navigation process may be detrimental to the blood vessel and to the health of the patient. Additionally, the physician may have to indicate which branch of the blood vessel may have to be used for further navigation which increases the criticality of the branching point. The determination of critical point(s) in the blood vessel provides identification of risks in the navigation pathway. Safety of the patient is ensured during the medical procedure. If the critical point is identified, at step 603, a new medical image is acquired by the imaging device. At step 604, a determination is made if calibration of the one or more subsequent images is to be performed. If a calibration is to be performed, the subsequent image is calibrated. If the calibration may not be required, the navigation is performed in the blood vessel using the calibrated medical image, at step 605.

Figure 5:
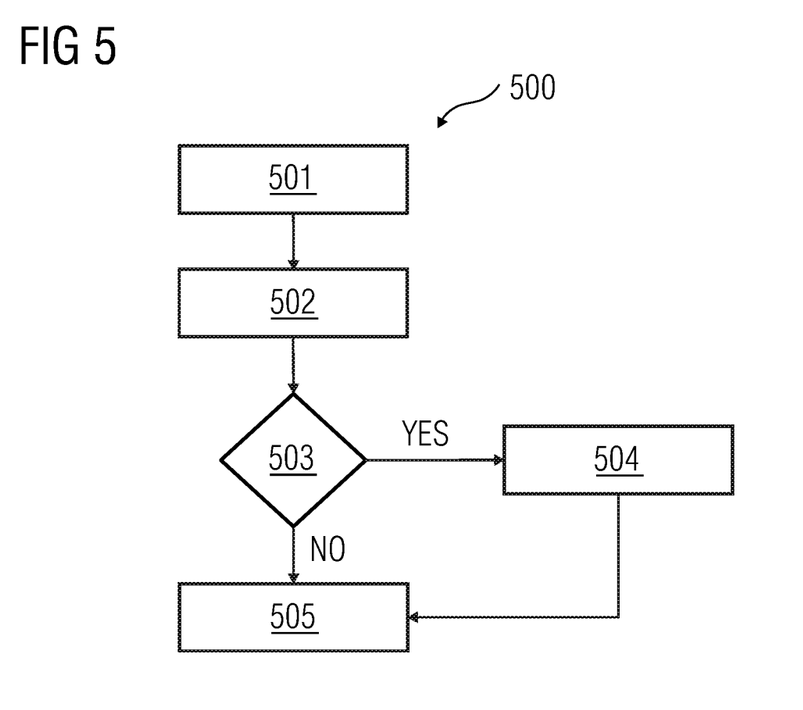
FIG. 5 depicts a flowchart of a method of calibrating one or more subsequent medical images based on the second modified medical image, according to an embodiment.

FIG. 5 depicts a flowchart of a method 500 of calibrating the one or more subsequent medical images based on the modified second medical image. At step 501, structural orientation of the one or more objects in the one or more subsequent medical image is determined. Determination of the structural orientation of the blood vessel provides accurate identification of the navigation pathway in the blood vessel. At step 502, a structural orientation of the one or more objects in the modified second medical image is determined. At step 503, a determination is made if a deviation exists between the structural orientation of the one or more objects in the one or more subsequent medical images and the one or more objects in the modified second medical image. The deviation may be identified, for example, using a pattern matching algorithm. If a deviation is identified, at step 504, the structural orientation of the one or more objects in the one or more subsequent medical image is corrected based on the structural orientation of the one or more objects in the modified second medical image.

In an embodiment, the one or more objects in the one or more subsequent medical images may be corrected by modifying the pixel values of one or more pixels in at least one portion of the one or more objects. The modification of pixel values in the one or more subsequent medical images may be performed based on the pixel values of the corresponding portion of the one or more objects in the second modified medical image. Modification of pixel values of the at least one portion of the one or more objects in the one or more subsequent medical image may perform scaling or warping of the one or more objects in the second medical image. At step 505, the modified subsequent medical image is used to perform the medical procedure of navigating the invasive medical instrument in the blood vessel. Alternatively, if no deviation is determined at step 503, the subsequent medical image may be used for the medical procedure without performing any modification. Modifying the one or more subsequent medical images with respect to the modified second medical image provides accurate navigation of the invasive medical instrument in the blood vessel. Modifying the subsequent medical image with respect to the second modified medical image prevents a physician from performing an erroneous motion of the invasive medical instrument in the blood vessel.

The modified subsequent medical image may be displayed on a display unit 106 to a physician such that navigation of the invasive medical instrument may be performed effectively in the blood vessel.

In an embodiment, the correction of the one or more objects in the subsequent medical images may be achieved using a suitable machine learning model. The machine learning model may be, for example, a neural network-based model that is configured to identify the deviation between the one or more objects in the second modified medical image and the one or more objects in the subsequent medical image. On identification of a deviation, the one or more objects in the subsequent medical image is corrected or modified using one or more machine learning techniques. The machine learning model may employ one or more machine learning techniques to perform the correction of the one or more objects in the subsequent medical image. In a further embodiment, the modified second medical image may be used for further training of the machine learning model to perform the modifications of one or more objects in one or more other medical images.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a navigation pathway for navigating an invasive medical instrument inside a blood vessel, the method comprising:
   receiving, by a processor, a first medical image associated with a patient, the first medical image acquired during a first medical imaging procedure;
   determining, by the processor, one or more parameters associated with the first medical image;
   identifying, by the processor, a second medical image from a plurality of images associated with the patient based on the determined one or more parameters, the second medical image acquired during a second medical imaging procedure performed prior to the first medical imaging procedure;
   determining, by the processor, deviation between a structural orientation of one or more objects in the first medical image and one or more objects in the second medical image;
   modifying, by the processor, the second medical image based on deviation between the structural orientation of the one or more objects in the first medical image and the one or more objects in the second medical image; and
   determining, by the processor, the navigation pathway for navigating the invasive medical instrument inside the blood vessel using the second medical image;
   wherein the navigation pathway corresponds to the modified structural orientation of the one or more objects in the second medical image.

2. The method of claim 1, wherein the one or more parameters associated with the first medical image comprises one or more of positions of a patient being imaged, position coordinates associated with an imaging device, angular position of the imaging device, and distance between a patient table and the imaging device.

3. The method of claim 1, wherein the second medical image is an image obtained from a medical database.

4. The method of claim 1, wherein identifying the second medical image based on the one or more parameters comprises:
   identifying, by the processor, one or more medical images based on the one or more parameters associated with the first medical image;
   identifying, by the processor, one or more objects from the first medical image;
   identifying, by the processor, one or objects from the one or more medical images;
   comparing, by the processor, the one or more objects in the first medical image and the one or more objects in the one or more medical images; and
   determining, by the processor, the second medical image from the one or more medical images based on the comparison.

5. The method of claim 1, wherein modifying the second medical image based on the first medical image comprises:
   determining, by the processor, a structural orientation of the one or more objects in the first medical image;
   determining, by the processor, a structural orientation of one or more objects in the second medical image;
   identifying, by the processor, a deviation between the structural orientation of the one or more objects in the first medical image and the one or more objects in the second medical image; and
   correcting, by the processor, the structural orientation of the one or more objects in the second medical image based on the structural orientation of the one or more objects in the first medical image if the deviation is identified.

6. The method of claim 1, further comprising:
   calibrating, by the processor, one or more subsequent medical images based on the modified second medical image, wherein the one or more subsequent medical images are acquired by an imaging device after acquisition of the second medical image by the imaging device; and
   determining, by the processor, from the calibrated one or more subsequent medical images a critical point in the navigation pathway in the blood vessel, by the processor.

7. The method of claim 6, further comprising:
   determining, by the processor, whether a new medical image is to be acquired by the imaging device based on the identification of the critical point in the navigation pathway.

8. The method of claim 6, wherein calibrating the one or more subsequent medical images based on the modified second medical image comprises:
   determining, by the processor, the structural orientation of one or more objects in the one or more subsequent medical images;
   determining, by the processor, the structural orientation of one or more objects in the modified second medical image;
   identifying, by the processor, a deviation between the structural orientation of the one or more objects in the one or more subsequent medical images and the one or more objects in the modified second medical image; and
   correcting, by the processor, the structural orientation of the one or more objects in the one or more subsequent medical images based on the structural orientation of the one or more objects in the modified second medical image if a deviation is identified.

9. The method of claim 1, wherein the first medical image is received from an imaging device and/or a medical database.

10. A system for determining a navigation pathway for navigating an invasive medical instrument inside a blood vessel, the system comprising:
    a processor;
    a medical database coupled to the processor;
    a memory coupled to the processor, the memory comprising a navigation module configured to:
    receive a first medical image associated with a patient;

determine one or more parameters associated with the first medical image;

identify a second medical image from a plurality of images associated with the patient based on the determined one or more parameters, the second medical image acquired during a medical imaging procedure prior to an acquisition of the first medical image;

determine deviation between a structural orientation of one or more objects in the first medical image and one or more objects in the second medical image;

modify the second medical image based on deviation between the structural orientation of the one or more objects in the first medical image and the one or more objects in the second medical image; and determine the navigation pathway for navigating the invasive medical instrument inside the blood vessel using the second medical image;

wherein the navigation pathway corresponds to the modified structural orientation of the one or more objects in the second medical image.

11. The system of claim 10, further comprising:
a patient table; and
an imaging device;
wherein the one or more parameters associated with the first medical image comprises one or more of positions of a patient being imaged, position coordinates associated with the imaging device, angular position of the imaging device, and distance between the patient table and the imaging device.

12. The system of claim 10, wherein the second medical image is an image obtained from the medical database.

13. The system of claim 10, wherein the navigation module is configured to:
identify one or more medical images based on the one or more parameters associated with the first medical image;
identify one or more objects from the first medical image;
identify one or objects from the one or more medical images;
compare the one or more objects in the first medical image and the one or more objects in the one or more medical images; and
determine the second medical image from the one or more medical images based on the comparison.

14. The system of claim 10, wherein the navigation module is configured to:
determine a structural orientation of the one or more objects in the first medical image;
determine a structural orientation of one or more objects in the second medical image;
determine a deviation between the structural orientation of the one or more objects in the first medical image and the one or more objects in the second medical image; and
correct the structural orientation of the one or more objects in the second medical image based on the structural orientation of the one or more objects in the first medical image if the deviation is identified.

15. The system of claim 10, wherein the navigation module is configured to:
calibrate one or more subsequent medical images based on the modified second medical image, wherein the one or more subsequent medical images are acquired by an imaging device after acquisition of the second medical image by an imaging device; and
determine from the calibrated one or more subsequent medical images a critical point in the navigation pathway in the blood vessel.

16. The system of claim 15, wherein the navigation module is configured to:
determine whether a new medical image is to be acquired by the imaging device based on the identification of the critical point in the navigation pathway.

17. A non-transitory computer implemented storage medium that stores machine-readable instructions executable by at least one processor determining a navigation pathway for navigating an invasive medical instrument inside a blood vessel, the machine-readable instructions comprising:
receiving a first medical image associated with a patient, the first medical image acquired during a first medical imaging procedure;
determining one or more parameters associated with the first medical image;
identifying a second medical image from a plurality of images associated with the patient based on the determined one or more parameters, the second medical image acquired during a second medical imaging procedure prior to the first medical imaging procedure;
determining deviation between a structural orientation of one or more objects in the first medical image and one or more objects in the second medical image;
modifying the second medical image based on deviation between the structural orientation of the one or more objects in the first medical image and the one or more objects in the second medical image; and
determining the navigation pathway for navigating the invasive medical instrument inside the blood vessel using the second medical image; wherein the navigation pathway corresponds to the modified structural orientation of the one or more objects in the second medical image.

* * * * *